United States Patent [19]

Ohkuma et al.

[11] 4,229,465
[45] Oct. 21, 1980

[54] CYANOPYRROLE DERIVATIVES

[75] Inventors: Kazuhiko Ohkuma; Hideo Takagi; Akira Nakata, all of Kanagawa; Shogo Kosaka, Hatano, all of Japan

[73] Assignee: Nippon Soda Company, Ltd., Tokyo, Japan

[21] Appl. No.: 55,321

[22] Filed: Jul. 6, 1979

[30] Foreign Application Priority Data

Jul. 10, 1978 [JP] Japan .................................. 53/83671

[51] Int. Cl.³ .................... C07D 207/44; A61K 31/40
[52] U.S. Cl. .............................. 424/274; 260/326.5 E
[58] Field of Search .................. 260/326.5 E; 424/274

[56] References Cited

U.S. PATENT DOCUMENTS 3,745,171  7/1973  Lockhart ..................... 260/326.5 E Primary Examiner—Jose Tovar
Attorney, Agent, or Firm—George B. Oujevolk

[57] ABSTRACT

Compounds of the general formula

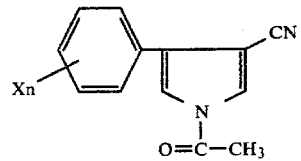

wherein
X is halogen, lower alkyl or lower haloalkyl, and
n is 0, 1 or 2;

are outstanding effective fungicides.

9 Claims, No Drawings

CYANOPYRROLE DERIVATIVES

DETAILED DESCRIPTION OF THE INVENTION

The present invention relates to novel cyanopyrrole derivatives, to a process for the preparation thereof and their uses as fungicides, in particular to fungicidally active compositions and method for controlling fungi.

It is already known that various 3-phenylpyrroles, for example, 3-(2-nitro-3-chlorophenyl)-4-chloropyrrole, 1-acetyl-3-(2-nitro-3-chlorophenyl)-4-chloropyrrole, 3-(3,4-dichlorophenyl)-4-chloropyrrole, have antibiotic activity and are useful as medicines.

It is also known that some 3-phenylpyrroles, for example, 3-(2-nitro-3-chlorophenyl)-4-chloropyrrole (Japanese Published Unexamined Patent Application No 88630/1976), 3-(3-trifluoromethylphenyl)-4-chloropyrrole (Japanese Published Examined Patent Application No. 2011/1975) are effective for the control of plant pathogens.

However, these known phenylpyrroles can not be used in agricultural application because the compounds are unstable against sunlight and their residual effects are low.

The inventors have studied the fungicidal activity of various 3-phenylpyrroles and have found that the cyanopyrroles of the formula [I].

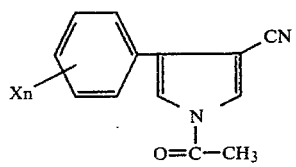

wherein
X is halogen, lower alkyl or lower haloalkyl, and
n is 0, 1 or 2,
have outstandingly superior fungicidal activity to the known 3-phenylpyrroles.

In the formula [I], X is preferably chlorine, bromine, trifluoromethyl or methyl. Most preferable compound in the formula [I] as fungicide for agricultural application is 1-acetyl-3-cyano-4-(2-chlorophenyl) pyrrole.

The compounds of this invention can be prepared by the reaction shown as follows:

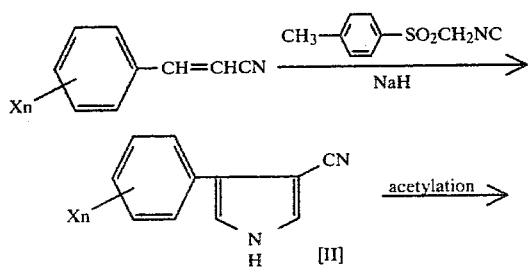

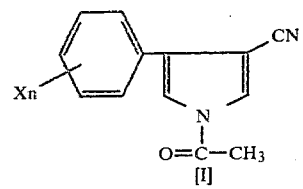

As shown above, the compound of this invention can be produced by a conventional acetylation reaction, namely by reacting a compound of the formula [II] with an acetylating agent. Acetic anhydride may be ordinarily used as the acetylating agent.

In the compound of the formula [II], the compound wherein n is zero, is known [Tetrahadron Letters (1972) 5337] although fungicidal activities thereof are not known, however, the other compounds are novel. The novel compounds of formula [II] may be prepared the same as the above mentioned known compound according to the above reaction equation.

The inventors found that also the compounds of formula [II] have fungicidal activity, although the activities are inferior to the compounds of this invention, acetylated compounds.

Typical compounds of this invention are shown in Table I.

TABLE I

| Compound No. | Chemical Structure Xn | Physical Constant (m.p.: °C.) |
|---|---|---|
| 1 | —(n=0) | 112–114 |
| 2 | 2-Cl | 106–107 |
| 3 | 3-Cl | 152–153 |
| 4 | 2,3-Cl$_2$ | 136–137 |
| 5 | 2-CF$_3$ | 67–69 |
| 6 | 2-Br | 99 . |
| 7 | 2-CH$_3$ | 114 |

Compound Nos. 8–14 of formula [II] correspond to the starting compounds for the compound Nos. 1~7 respectively, and their physical constants are as follows:

| Compound No. | Physical Constant (m.p.: °C.) |
|---|---|
| 8 | 129–131 |
| 9 | 137–139 |
| 10 | 147 |
| 11 | 153 |
| 12 | 105–107 |
| 13 | 145 |
| 14 | 115–118 |

The following examples illustrate the preparation of compounds according to the invention:

EXAMPLE 1

1-acetyl-3-cyano-4-phenylpyrrole (Compound No. 1)

4 g of 3-cyano-4-phenylpyrrole (Compound No. 8) was added to 20 ml of acetic anhydride and heated for 4 hours in oil-bath of 140°–150° C. After cooling, the resulting reaction mixture was poured into about ten-times volume of cold water to decompose excess acetic anhydride. The resulting precipitate was filtrated, washed with water and dried to obtain 4.5 g of crystal. The crystal was recrystallized from methyl alcohol to obtain 3 g of the desired product.

Colorless crystal, m.p. 112°–114° C.

EXAMPLE 2

1-acetyl-3-cyano-4-(2-chlorophenyl) pyrrole
(Compound No. 2)

7 g of sodium hydride (50% oil suspension) was added to 200 ml of anhydrous ether and suspended by stirring. To the suspension were dropwisely added 20 g of o-chloro-cinnamic nitrile and a solution of 23.9 g of tosylmethyl isocyanide in 400 ml of anhydrous ether and 200 ml of anhydrous dimethylsulfoxide under stirring. After the addition, stirring was continued for 30 minutes, and then the mixture was poured into 1.2 l of ice-cold water. Water layer was separated from ether layer and was twice extracted with 300 ml of ethyl acetate. The ether layer and the ethyl acetate layer was mixed, and the mixed solution was washed with aqueous sodium chloride. After drying, the solution was evaporated to dryness under reduced pressure to obtain crude crystal. The crude crystal was washed with benzene to obtain 16.5 g of 3-cyano-4-(2-chlorophenyl) pyrrole (Compound No. 9).
m.p. 137°–139° C.

10 g of the compound No. 9 was mixed with 40 ml of acetic anhydride and heated for 3 hours in an oil-bath (140°–150° C.). After cooling, the resulting reaction mixture was poured into ice-cold water and stirred to decompose excess acetic anhydride. Precipitated crystal was separated by filtration, washed with water and recrystallized from methyl alcohol to obtain 8.5 g of the desired product.

Pale grayish green plates, m.p. 106°~107° C.
I.R. absorption (cm$^{-1}$): 3080, 2220, 1728, 1515, 1360, 1320, 1260, 1220, 1180, 1080, 945, 830, 763.

EXAMPLE 3

1-acetyl-3-cyano-4-(2,3-dichlorophenyl) pyrrole
(Compound No. 4)

792 mg of 2',3'-dichloro-cinnamic nitril was reacted with 780 mg of tosylmethyl isocyanide as in Example 2 to obtain 235 mg of 3-cyano-4-(2,3-dichlorophenyl) pyrrole (Compound No. 11).
m.p. 153° C.

100 mg of the compound No. 11 was reacted with 2 ml of acetic anhydride as in Example 2 to obtain 74 mg of the desired product.

Pale brown needles, m.p. 136°–137° C.

EXAMPLE 4

1-acetyl-3-cyano-4-(2-trifluoromethylphenyl) pyrrole
(Compound No. 5)

788 mg of o-trifluoromethyl cinnamic nitrile was reacted with 780 mg of tosylmethyl isocyanide as in Example 2 to obtain 200 mg of 3-cyano-4-(2-trifluoromethylphenyl) pyrrole (Compound No. 12).
m.p. 105°–107° C.

100 mg of the compound No. 12 was reacted with 2 ml of acetic anhydride as in Example 2 to obtain 76 mg of the desired product.
m.p. 67°–69° C.

The compounds of the invention possess excellent fungicidal activity when employed to prevent damage to plants, in particular, the compounds possess outstanding residual activity.

The compound may be used directly without mixing with carriers.

The active ingredient of a fungicidal composition according to the invention may be formulated by mixing with suitable carriers in a form generally used in pesticidal compositions, such as wettable powder, emulsifiable concentrate and dust formulation. As solid carriers, bentonite, diatomaceous earth, apatite, gypsum, talc, pyrophyllite, vermiculite and clay, for example, may be useds liquid carriers, kerosene, mineral oil, petroleum, solvent naphtha, xylene, cyclohexane, cyclohexanone, dimethylformamide, dimethylsulfoxide, alcohol, acetone, benzene and water, for example, may be used. If so desired, a surface active agent may be added in order to give a homogeneous and stable formulation.

The concentration of the active ingredient in the fungicidal composition may vary according to type of formulation, and is for example, 5 to 80 weight percent, preferably 20 to 80 weight percent, in wettable powders; 5 to 70 weight percent, preferably 10 to 50 weight percent, in emulsifiable concentrates; and 0.5 to 20 weight percent, preferably 1 to 10 weight percent, in dust formulation.

Furthermore, the compounds may be used in mixture with other fungicides, insecticides, acaricides and herbicides.

Some non-limiting examples of fungicidal compositions according to the invention are as follows:

EXAMPLE 5

| Wettable Powder | |
| --- | --- |
| | Parts by weight |
| Compound No. 1 | 20 |
| Diatomaceous earth | 73 |
| Sodium higheralkyl sulfate | 7 |

These components were mixed homogeneously and reduced to fine particles to provide a wettable powder containing 20% of the active ingredient.

EXAMPLE 6

| Emulsifiable Concentrate | |
| --- | --- |
| | Parts by weight |
| Compound No. 2 | 20 |
| Xylene | 42 |
| Dimethylformamide | 30 |
| Polyoxyethylene alkylphenyl ether | 8 |

These ingredients were mixed and dissolved to provide an emulsifiable concentrate containing 20% of the active ingredient.

| Dust Formulation | |
| --- | --- |
| | Parts by weight |
| Compound No. 3 | 2 |
| Talc | 98 |

These ingredients were mixed homogeneously and reduced to fine particles to provide a dust formulation containing 2% of the active ingredient.

The wettable powder or the emulsifiable concentrate is diluted with water to a desired concentration and used as a suspension or emulsion for treating soil, plant or seed. The dust formulation is directly used for treating soil, plant or seed.

The fungicides of the present invention are effective for the control of many plant diseases, for example, by applying the fungicides to plants, gray mold and Schlerotinia rot of vegetables, leaf mold of tomato, anthracnose, Fusarium wilt and gummy stem blight of cucumber, blast, sheath light and Helminthosporium leaf spot of rice, stripe of barley, black spot of pear, brown rot of peach, gray mold of grape and scab of apple can be controlled. By treating soil, anthracnose, Fusarium wilt and gummy stem blight of cucumber can be controlled. By treating seeds, blast and Helminthosporium leaf spot of rice, bunt of wheat and stripe of barley can be controlled.

The fungicidal effect of the compounds of this invention is illustrated by the following tests:

TEST 1

Test for Control of Gray Mold of Bean

Detached leaves of kindney beans (*Phaseolus vulgaris*) were immersed for about 30 seconds in aqueous suspensions prepared by diluting a wettable powder to different concentrations of test compound. After air drying, the treated leaves were inoculated with mycelia of *Botrytis cinerea* and kept at 20° C. in a moist chamber. Control effect was determined 4 days after inoculation. The results are shown in Table 2. Phyto-toxicity was not observed.

TABLE 2

| | Concentration of Active Ingredient (ppm) | Control Value (%) |
|---|---|---|
| Test Compound No. | | |
| 1 | 50 | 100 |
| 2 | 50 | 100 |
| 3 | 50 | 100 |
| 4 | 50 | 100 |
| 5 | 50 | 100 |
| 6 | 50 | 100 |
| 7 | 50 | 100 |
| Comparative Compound* | | |
| 1 | 50 | 100 |
| 2 | 50 | 80 |

*Comparative Compound
1 3-chloro-4-(2-nitro-3-chlorophenyl) pyrrole (Japanese Published Unexamined Patent Application No. 88630/1976)
2 Euparen (Trade name): N'-dichlorofluoromethylthio-N,N-dimethyl-N'-phenylsulfamide

TEST 2

Test for Control of Gray Mold of Bean (residual effect)

Potted kidney bean (*Phaseolus vulgaris* L.) seedlings which was grown for about 3 weeks were sprayed once with a chemical solution at a concentration of 200 ppm of active ingredient and then kept in a greenhouse. The leaves were detached and inoculated with mycelium of *Botrytis cinerea* 7 days after spraying and kept in a moist chamber at 20° C. Control effect was determined 4 days after inoculation. The results are shown in Table 3. Phyto-toxicity was not obserbed.

TABLE 3

| Test Compound No. | Control value (%) |
|---|---|
| 1 | 100 |
| 2 | 100 |
| 3 | 93 |
| 4 | 100 |
| 5 | 90 |
| 6 | 89 |
| 7 | 87 |
| Comparative Compound* | |
| 1 | 0 |
| 2 | 48 |
| 3 | 0 |
| 4 | 53 |

*Comparative Compound
1 and 2: the same as in Test 1.
3: 4-chloro-3-(3,4-dichlorophenyl)pyrrole (Japanese Published Examined Patent Application No.6748/1967)
4: 4-chloro-3-(3-trifluoromethylphenyl)pyrrole Japanese Published Examined Patent Application No. 2011/1975)

We claim:
1. A compound of the general formula

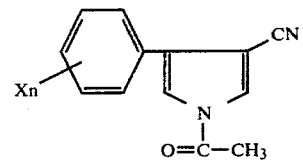

wherein X is chlorine, bromine, methyl or trifluoromethyl, and n is 0, 1 or 2.

2. A compound according to claim 1, wherein X is chlorine.

3. A compound according to claim 2, wherein X is 2-Cl and n is 1.

4. A fungicidal composition comprising an inert carrier and a fungicidally effective amount of a compound of claim 1.

5. A fungicidal composition comprising an inert carrier and a fungicidally effective amount of a compound of claim 2.

6. A fungicidal composition comprising an inert carrier and a fungicidally effective amount of a compound of claim 3.

7. A method for the control of fungi comprising applying to the locus to be protected an effective amount of a compound of claim 1.

8. A method for the control of fungi comprising applying to the locus to be protected an effective amount of a compound of claim 2.

9. A method for the control of fungi comprising applying to the locus to be protected an effective amount of a compound of claim 3.

* * * * *